United States Patent
Talbot et al.

(10) Patent No.: US 10,401,653 B2
(45) Date of Patent: Sep. 3, 2019

(54) METHOD AND DEVICE FOR AIDING THE CHOICE OF A PIECE OF EQUIPMENT COMPRISING AT LEAST ONE OPHTHALMIC LENS AND A FRAME, METHOD AND DEVICE FOR SELECTING SUCH A PIECE OF EQUIPMENT

(71) Applicant: ESSILOR INTERNATIONAL (COMPAGNIE GENERALE D'OPTIQUE), Charenton-le-Pont (FR)

(72) Inventors: Deborah Talbot, Charenton-le-Pont (FR); Christine Jouvanceau, Charenton-le-Pont (FR); Celine Torracinta, Charenton-le-Pont (FR); Ahmed Haddadi, Charenton-le-Pont (FR); Sylvie Mouchon, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 195 days.

(21) Appl. No.: 15/121,267

(22) PCT Filed: Feb. 24, 2015

(86) PCT No.: PCT/FR2015/050445
§ 371 (c)(1),
(2) Date: Aug. 24, 2016

(87) PCT Pub. No.: WO2015/128577
PCT Pub. Date: Sep. 3, 2015

(65) Prior Publication Data
US 2016/0363788 A1   Dec. 15, 2016

(30) Foreign Application Priority Data
Feb. 28, 2014 (FR) ..................... 14 51652

(51) Int. Cl.
*A61B 3/14* (2006.01)
*G02C 13/00* (2006.01)
*A61B 3/11* (2006.01)

(52) U.S. Cl.
CPC ............ *G02C 13/005* (2013.01); *A61B 3/111* (2013.01); *A61B 3/14* (2013.01)

(58) Field of Classification Search
CPC ............ A61B 3/14; A61B 3/111; A61B 3/112
(Continued)

(56) References Cited

U.S. PATENT DOCUMENTS

| 2010/0128220 A1 | 5/2010 | Chauveau |
| 2010/0296055 A1 | 11/2010 | Esser et al. |
| 2015/0109577 A1* | 4/2015 | Haddadi .................. A61B 3/11 351/204 |

FOREIGN PATENT DOCUMENTS

| EP | 2134249 B1 | 2/2013 |
| WO | 93/20744 A1 | 10/1993 |

(Continued)

OTHER PUBLICATIONS

International Search Report, dated May 27, 2016, from corresponding PCT Application.

*Primary Examiner* — Hung X Dang
(74) *Attorney, Agent, or Firm* — Young & Thompson (57) ABSTRACT

A method for aiding the choice, by a future wearer, of a piece of visual equipment including at least one ophthalmic lens and a spectacle frame, includes the following steps: receiving at least first and second data items representative of first and second distances measured between an eye of the wearer and the frame; determining a first width and a second width, associated with the first data item and the second data item, respectively, by comparing, for each data item, the lower and upper limits of a range of values associated with the distance represented by the data item in question; and constructing an (Continued)

image including a first portion having the first width and a second portion having the second width, the first portion and the second portion being juxtaposed in the image. A method allowing a future wearer to select such a piece of equipment is also described.

16 Claims, 3 Drawing Sheets

(58) Field of Classification Search
USPC .................................................. 351/204, 246
See application file for complete search history.

(56) References Cited

FOREIGN PATENT DOCUMENTS

| WO | 01/62139 A1 | 8/2001 |
|---|---|---|
| WO | 2007/056797 A1 | 5/2007 |

\* cited by examiner

METHOD AND DEVICE FOR AIDING THE CHOICE OF A PIECE OF EQUIPMENT COMPRISING AT LEAST ONE OPHTHALMIC LENS AND A FRAME, METHOD AND DEVICE FOR SELECTING SUCH A PIECE OF EQUIPMENT

TECHNICAL FIELD OF THE INVENTION

The present invention relates to procedures for selecting optical articles.

It more particularly relates to a method and device for selecting a piece of visual equipment comprising at least one ophthalmic eyeglass and a frame, and to a method and device for accompanying the choice of such a piece of equipment.

PRIOR ART

During the choice of a piece of visual equipment, such as a pair of spectacles, comprising a frame and corrective eyeglasses, in the shop of an optician, the future wearer of this piece of equipment is in general guided by his esthetic tastes as regards the frame and the advice of the optician as regards certain technical aspects.

From the technical point of view, the number of parameters at play is however quite large (parameters for example used to describe the shape of the frame and its position with respect to the face of the wearer). It is therefore difficult for the optician to objectively take into account all of these parameters and to make the wearer aware of the situation in all its complexity.

Systems for taking measurements have been proposed, such as for example described in patent application EP 2 134 249, in order to improve the objective analysis of the situation, especially of the position of a frame (and therefore of the corrective eyeglasses) with respect to the face (and therefore to the eyes) of the wearer and of individual behavioral parameters.

The raw numbers obtained by these measurements are however quite abstruse and do not allow a dialogue to be established between the optician and the wearer on these technical aspects and the conclusions that it is possible to draw therefrom.

SUBJECT OF THE INVENTION

In this context, the present invention proposes a method allowing a future wearer to select a piece of visual equipment comprising at least one ophthalmic eyeglass and a frame, comprising the following steps:
  measuring, by means of a measurement-taking device, the value of a characteristic parameter that is characteristic of a posture or of a behavior of the wearer, and/or that is characteristic of the position of the frame on the wearer;
  constructing an image comprising a first portion containing said characteristic parameter and a second portion placing the measured value in a range of values that is bounded by a lower bound and an upper bound.

Thus, the measured value is located in a range of values, thereby allowing the wearer to better understand to what the measured value corresponds; the parameter contained in the first portion (for example taking the form of a graphical representation of the parameter) furthermore allows the wearer to understand what is represented by this parameter.

Provision is for example made for a step of displaying the constructed image on a screen.

The upper bound and the lower bound may respectively be the maximum value and the minimum value of the characteristic parameter encountered in a given population, these values for example being stored in an optionally remote database.

According to one envisionable embodiment, the constructing step is implemented by a remote computer and a programmable device, for example located in the shop, sends said measured value to the remote computer and receives the constructed image from the remote computer for display.

This makes it possible to decrease the processing carried out in the shop and therefore the power of the means required to do this processing.

As a variant, all of the processing, namely especially the steps of measuring and constructing, may be carried out by a programmable apparatus located in the shop.

The invention also proposes a method for accompanying the choice of a piece of equipment comprising at least one ophthalmic eyeglass and a spectacle frame by a future wearer of this piece of equipment, comprising the following steps:
  a step in which at least one first datum representative of a first distance measured between one eye of the wearer and the frame, and a second datum representative of a second distance measured between the eye of the wearer and the frame, are received (by an electronic apparatus);
  a step in which a first width and a second width, respectively associated with the first datum and the second datum, are determined (by the electronic apparatus) by comparing each datum to the lower and upper bounds of a range of values that is associated with the distance represented by the datum in question;
  a step in which an image comprising a first section having the first width and a second section having the second width is constructed, the first section and the second section being juxtaposed in the image.

Such an image allows the wearer to understand where the first and second distances each lie in a range of values (for example the values encountered in a given population), thereby improving his perception of the situation with respect to the raw data of the values in question.

The first distance is for example a distance, along a horizontal axis parallel to a sagittal plane of the wearer, between the eye rotation center of the wearer and a point of the frame or a positional point of a corrective eyeglass of said eye in the frame.

The aforementioned eye is for example the left eye of the wearer; provision may then be made for the first section to be an annular section for example formed in a first angular sector located in a left-hand portion of the image, and for the second section to be an annular section for example formed in a second angular sector located in a left-hand portion of the image.

Provision may be made as a variant for the first annular section and the second annular section to be located in the right-hand portion of the image.

The constructed image for example comprises an annulus-shaped graduated scale the outside radius of which may correspond to the upper bound of the range of values that is associated with the first distance in the first angular sector and to the upper bound of the range of values that is associated with the second distance in the second angular sector. The annular sections are thus represented on a graduated scale that represents distinct values depending on the datum in question.

The receiving step may furthermore comprise the reception of a third datum representative of a third distance measured between the right eye of the wearer and the frame and of a fourth datum representative of a fourth distance measured between the right eye of the wearer and the frame.

The determining step may for its part comprise determining a third width and a fourth width, respectively associated with the third datum and the fourth datum, by comparing each datum to the lower and upper bounds of a range of values that is associated with the distance represented by the datum in question.

The constructed image may then comprise a third annular section having the third width in a third angular sector located in a right-hand portion of the image and a fourth annular section having the fourth width in a fourth angular sector located in the right-hand portion of the image.

According to the variant envisioned above, the third annular section and the fourth annular section may be located in the left-hand portion of the image.

Thus, whatever the adopted representation, data relating to one eye will figure on one side of a vertical axis of the image, whereas data relating to the other eye will feature on the other side of this vertical axis.

The method may furthermore comprise a prior step of measuring the first distance and second distance by means of a measurement-taking device and/or a step of displaying the constructed image on a screen.

Provision may be made, for each of the first and second distances, for the upper and lower bounds of the range of values that is associated with the distance in question to be able to be respectively the maximum value and the minimum value of the distance in question encountered in a given population. The maximum and minimum values are for example stored in a remote database, as explained below.

The second distance is for example a distance between the pupil of the eye of the wearer and a median point of the frame along a horizontal axis perpendicular to the sagittal plane of the wearer.

Provision may be made for the fourth distance to be a distance between the pupil of the right eye and the median point of the frame along the horizontal axis perpendicular to the sagittal plane of the wearer; the second angular sector and the fourth angular sector are located on either side of a horizontal direction of the image.

Provision may also be made for:
the receiving step to comprise the reception of a fifth datum representative of a fifth distance measured between the left eye of the wearer and the frame and of a sixth datum representative of a sixth distance measured between the right eye of the wearer and the frame, for
the determining step to comprise determining a fifth width and a sixth width, respectively associated with the fifth datum and the sixth datum, by comparing each datum to the lower and upper bounds of a range of values that is associated with the distance represented by the datum in question, and for
the constructed image to comprise a fifth annular section having the fifth width in a fifth angular sector located in the left-hand portion of the image and a sixth annular section having the sixth width in a sixth angular sector located in the right-hand portion of the image.

The fifth distance is for example a distance between the pupil of the left eye and a predefined point of the frame along a vertical axis and the sixth distance is for example a distance between the pupil of the right eye and the predefined point of the frame along said vertical axis.

The image may furthermore comprise a circular arc the angular extent of which is determined by a characteristic angle of the frame. The characteristic angle represents the tilt of the frame (pantoscopic angle) or the wrap of the frame.

The constructed image may furthermore comprise, for example in a central zone (on the disk located at the center of the annulus in the example described below), the representation on an orthonormal coordinate system of the coordinates of the eye rotation center, for example with respect to the frame.

The steps of receiving, determining and constructing may be implemented by a remote computer and a programmable device, which is for example located in the shop, may then send the first datum and the second datum to the remote computer and receive the constructed image from the remote computer for display on a screen, which is for example located in the shop.

As a variant, all of the operations could be carried out in the shop.

The steps of the methods described above are for example implemented by an electronic apparatus, for example a programmable apparatus, or by a plurality of apparatuses of this type, such as described in the description given below.

The invention also proposes a device for selecting a piece of equipment comprising at least one ophthalmic eyeglass and a frame, comprising:
a module for determining a datum representative of the value of a characteristic parameter that is characteristic of a posture or of a behavior of the wearer, or that is characteristic of the position of the frame on the wearer;
a module for constructing an image comprising a first portion containing said characteristic parameter and a second portion placing the measured value in a range of values that is bounded by a lower bound and an upper bound. Lastly, the invention proposes a device for accompanying the choice of a piece of equipment comprising at least one ophthalmic eyeglass and a spectacle frame by a wearer, comprising:
a module for receiving at least one first datum representative of a first distance measured between one eye of the wearer and the frame, and a second datum representative of a second distance measured between the eye of the wearer and the frame;
a module for determining a first width and a second width, respectively associated with the first datum and the second datum, by comparing each datum to the lower and upper bounds of a range of values that is associated with the distance represented by the datum in question;
a module for constructing an image comprising a first section having the first width and a second section having the second width, the first section and the second section being juxtaposed in the image.

DETAILED DESCRIPTION OF AN EXEMPLARY EMBODIMENT

The description which follows with reference to the appended drawings, which are given by way of nonlimiting examples, will make it easy to understand the essence of the invention and how it can be achieved.

Figure 1:
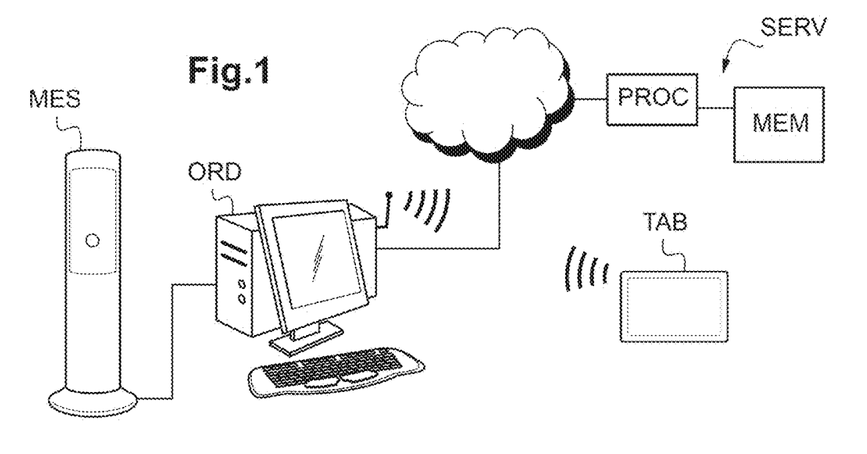
FIG. 1 shows an IT system via which the invention is implemented.

In the appended drawings:

FIG. 1 shows an IT system via which the invention is implemented. This IT system is for example distributed between a shop for selling optical articles, especially spectacle frames, and a remote location where a remote server SERV is located.

In the shop, the system especially comprises a measurement-taking device MES, a computer ORD and a tablet TAB. The remote server SERV for its part comprises a processor PROC and storing means MEM, such as a hard disk.

The various devices of the system are connected by (wired or wireless) communication means and may thus exchange data, especially those mentioned in the description below. In the example described here, the measurement-taking device MES is linked to the computer ORD by means of a wired link (for example an Ethernet cable), the tablet TAB is linked to the computer ORD by means of a wireless link (for example via a wireless local area network or WLAN) and the remote server SERV is linked to the computer ORD via a computer network (for example the Internet).

In the present embodiment, each device takes the form of a programmable apparatus based on a microprocessor-centric architecture: the steps implemented by the device in question result from the execution, by the microprocessor of the device in question, of the instructions of a computer program stored in the device. However, the invention is not limited to such devices and could also be implemented by means of dedicated electronic devices, for example functioning under the command of application-specific integrated circuits (ASICs).

The measurement-taking device MES is for example of the type described in patent application EP 2 134 249. When a future wearer of the new piece of visual equipment to be defined places his face in front of the device, the measurement-taking device MES measures various geometrico-morphological parameters and especially those mentioned below. When the future wearer is already wearing an old piece of visual equipment (on which a measuring clip and/or in which eyeglasses are optionally mounted), the measured parameters especially include characteristic parameters that are characteristic of the frame of this old piece of equipment and/or of the relative position of the frame and at least one eye of the wearer.

The processor PROC of the server SERV manages a remote database stored in the storing means MEM. This database contains data representative of previously measured values of the various aforementioned parameters, for example for all the cases treated in a given shop, in a group of shops, or at a regional, national or even global level.

The tablet TAB comprises a touch screen on which various images intended for the optician and/or the wearer present in the shop are to be displayed; the touch screen may furthermore be used to input commands of the user, here in general the optician, such as commands to pass from one image to another.

Figures 2, 3:
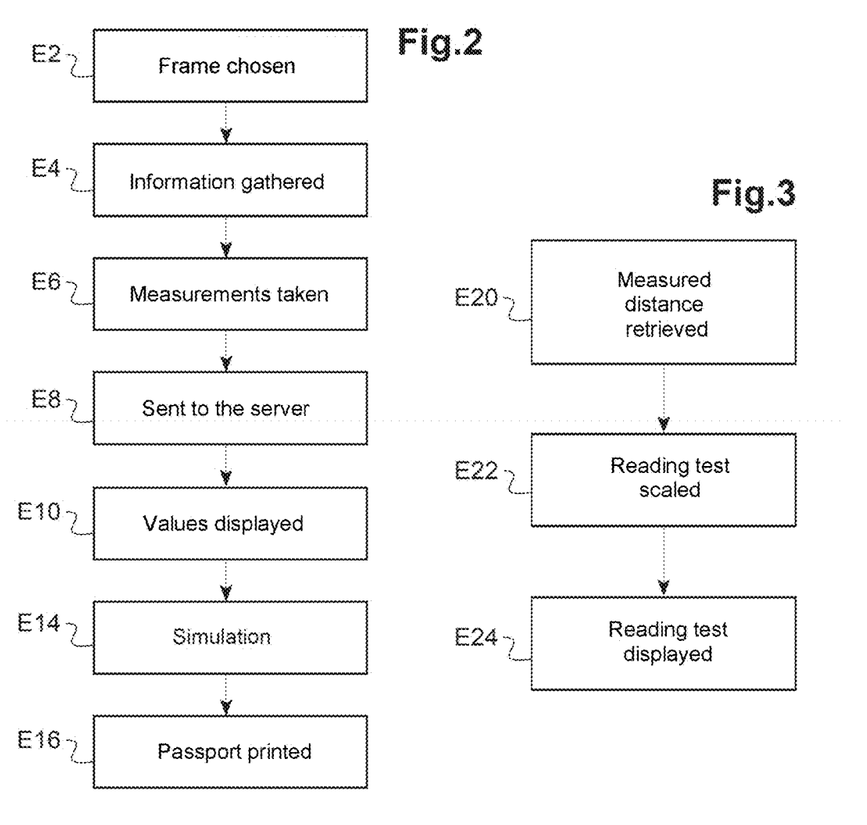
FIG. 2 shows a procedure allowing a wearer to select a pair of spectacles in a shop equipped with such a system.
FIG. 3 shows a method for displaying a reading test of suitable size.

FIG. 2 shows a procedure allowing a future wearer to select a pair of vision-correcting spectacles in a shop equipped with a system such as that presented above with reference to FIG. 1.

The wearer arrives in the shop with a prescription for corrective eyeglasses (which define a correction for the right eye and a correction for the left eye).

The wearer then chooses at least one frame from the frames displayed in the shop depending on his tastes (step E2). The optician may then indicate in this step that certain frames will not be suitable for the required corrections.

When the wearer has chosen at least one frame, he may optionally be asked to fill in a questionnaire (step E4) in order to allow the optician to obtain information on the wearer, especially information on his customary activities (for example whether the wearer practices sports or reads regularly), that could have an influence on the choice of frame (especially if the wearer has chosen a plurality of frames in step E2) or on the choice of eyeglasses.

The frame chosen by the wearer is then equipped with a measuring clip and the wearer places himself facing the measurement-taking device MES with the frame positioned on his face.

The measurement-taking device MES then determines (step E6) the values of the following parameters:
- for each eye, the (horizontal) distance between the pupil of the eye in question and the center of the frame (monocular pupillary distance), along a horizontal axis perpendicular to the sagittal plane of the wearer;
- for each eye, the vertical distance (height) between the pupil of the eye in question and the bottom of the frame;
- for each eye, the (horizontal) distance between the eye rotation center (ERC) and the eyeglass borne by the frame (or the place that the eyeglass is intended to occupy when no eyeglass is mounted), along a horizontal axis parallel to the sagittal plane;
- the tilt (in general represented by the pantoscopic angle) of the frame;
- the wrap (or "le galbe" to use the French term) of the frame;
- the dominant eye of the wearer;
- the behavior of the wearer when following a movement (eye mover vs head mover).

It will be noted that the first three parameters amount to defining the coordinates of the eye rotation center (ERC) in an orthonormal coordinate system attached to the frame.

The wearer then possibly positions himself in a natural reading position, so that the measurement-taking device MES can for example measure a reading distance and a value representative of the inclination of the gaze of the wearer in this reading position, for example the angle of vertical inclination of the head of the wearer.

Data representative of the various measured values are then sent to the remote server SERV in step E8, for example in association with an identifier of the wearer.

These data are on the one hand stored in the aforementioned remote database and thus enrich it.

These data are moreover used to construct various images to be displayed on the screen of the tablet TAB in a step E10, as explained below. In the example described here, the images are constructed by the processor PROC in the remote server SERV, then transmitted to the tablet TAB for display. As a variant, the images could be constructed by the computer ORD or the tablet TAB (and transmitted to the tablet TAB from the computer ORD in the first case). In this variant, the computer ORD or the tablet TAB may communicate with the remote server SERV in order to learn in real time the minimum and maximum values of the various parameters in the remote database (values used in the construction of the image as explained below).

The user (in general the optician) may pass from one image to the next, for example by sliding a finger over the touchscreen of the tablet TAB.

Figure 4:
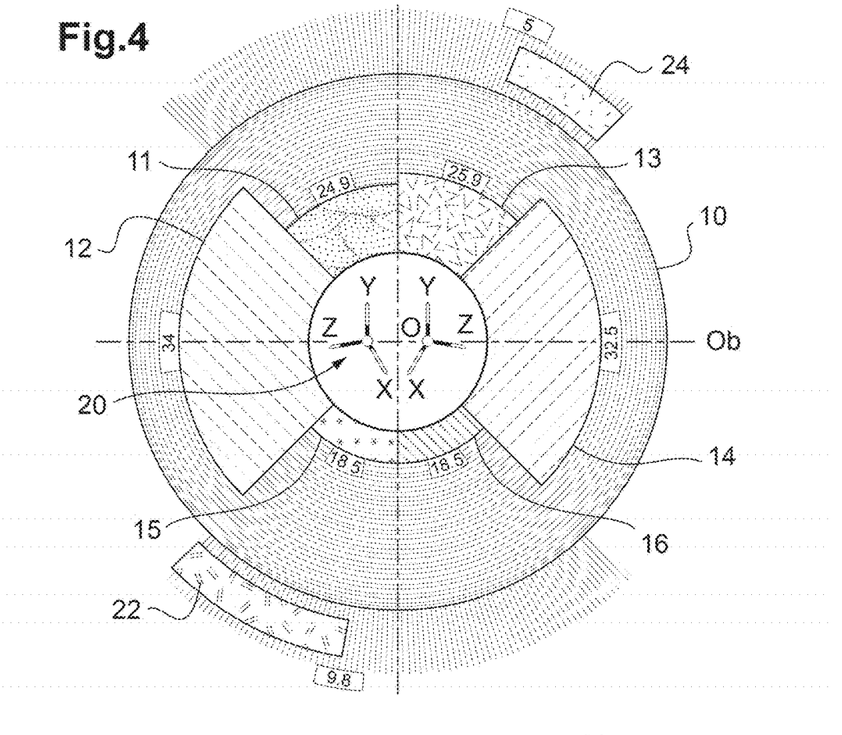
FIG. 4 shows a first exemplary image to be displayed on the screen of a tablet of the system in FIG. 1.

A first exemplary image to be displayed on the screen of the tablet TAB is shown in FIG. 4.

This image especially presents the various aforementioned eye-frame distances for the right eye and left eye in an annulus 10, centered on a point O, of inside radius $R_i$ and of outside radius $R_e$. For the sake of clarity of the description, mention will be made of the horizontal axis of the image passing through the point O (Oa below) and of the vertical axis of the image passing through the point O (Ob below) although these axes are not shown in the image in the example described here.

In the interior of the annulus 10, one angular sector is associated around the point O with each represented parameter. More precisely, in the example illustrated in FIG. 4:
- a first angular sector located in the left-hand portion of the image (i.e. on the left of the vertical axis Ob), here extending over 45° from the axis Ob in the upper portion of the image (i.e. above the axis Oa), is associated with the horizontal distance between the rotation center of the left eye and the corresponding eyeglass borne by the frame;
- a second angular sector located in the left-hand portion of the image, here extending over 90° on either side of the horizontal axis Oa, is associated with the horizontal distance between the pupil of the left eye and the center of the frame;
- a third angular sector located in the right-hand portion of the image (i.e. on the right of the vertical axis Ob), here extending over 45° from the axis Ob in the upper portion of the image (i.e. above the axis Oa), is associated with the horizontal distance between the rotation center of the right eye and the corresponding eyeglass borne by the frame;
- a fourth angular sector located in the right-hand portion of the image, here extending over 90° on either side of the horizontal axis Oa, is associated with the horizontal distance between the pupil of the right eye and the center of the frame;
- a fifth angular sector located in the left-hand portion of the image, here extending over 45° from the vertical axis Ob in the lower portion of the image (i.e. below the axis Oa), is associated with the vertical distance between the pupil of the left eye and the frame;
- a sixth angular sector located in the right-hand portion of the image, here extending over 45° from the vertical axis Ob in the lower portion of the image, is associated with the vertical distance between the pupil of the left eye and the frame.

For each of these parameters, the value $V_{mes}$ measured in step E6 has been represented by the width L (i.e. the difference between the outside radius and the inside radius) of an angular section centered on the point O and located in the angular sector associated with the parameter in question. The inside radius of each annular section is here equal to the inside radius $R_i$ of the annulus 10.

The width L is determined with respect to a minimum value $V_{min}$ and to a maximum value $V_{max}$ of the parameter in question. These minimum and maximum values $V_{min}$, $V_{max}$ are for example the minimum and maximum values encountered for the parameter in question among those values of this parameter which are stored in the database of the remote server SERV. As already indicated, these values may correspond to various populations, for example to the wearers of one shop, to the wearers on the scale of a country or to all the wearers for whom measurements have been carried out (whatever the geographical region). They may furthermore in this case vary as measurements are carried out (step E6) and stored in the server SERV (step E8). As a variant, the minimum and maximum values could be predefined fixed values.

The width L is for example determined linearly between the inside radius $R_i$ of the annulus (which corresponds here to the value $V_{min}$) and the outside radius $R_e$ of the annulus (which corresponds here to the value $V_{max}$), i.e. by the formula: $L=R_i+(R_e-R_i)\cdot(V_{mes}-V_{min})/(V_{max}-V_{min})$. Provision may however be made for the width L not to vary linearly with the measured value $V_{mes}$ (for example in order to better highlight differences in the level of a given value of the parameter).

Thus, an image is constructed that comprises, for each of the six parameters mentioned above, an annular section of width L (determined as just described) extending (from the inside radius $R_i$ of the annulus) in the angular sector associated with the parameter in question:
- a first annular section 11 extends in the first angular sector;
- a second annular section 12 extends in the second angular sector;
- a third annular section 13 extends in the third angular sector;
- a fourth annular section 14 extends in the fourth angular sector;
- a fifth annular section 15 extends in the fifth angular sector;
- a sixth annular section 16 extends in the sixth angular sector.

Provision may furthermore be made to include, in the image, a numerical representation of the value measured for the various parameters, said representation for example being placed level with the outside radius of the annular section associated with the parameter in question. Moreover, the various annular sections may be colored, with one color associated with each annular section.

When the image is displayed on the screen of the tablet TAB, the wearer and the optician have at their disposal an easily understandable and everyday representation of the various parameters, thereby allowing them to easily discuss how suitable the piece of frame-eyeglasses equipment is for the wearer. Furthermore, in the described example, the measured values are represented in comparison to values encountered (in real time) in a given population, thereby providing the optician and the wearer with aggregated information that is more complete and more easily understandable than a raw value (especially by virtue of the possible comparative reference to minimum and maximum values, or to a given population).

In the image illustrated in FIG. 4, provision is furthermore made to include, in the interior of the annulus (i.e. in the disk of center O and of radius $R_i$), a representation 20 in perspective of an orthonormal coordinate system for each eye. On each axis of the orthonormal coordinate system, the measured value $V_{mes}$ of the parameter associated with the axis in question (from among the parameters giving the coordinates of the eye rotation center with respect to the frame as indicated above) has been shown by darkening or coloring a proportion of the shown axial segment equal to $(V_{mes}-V_{min})/(V_{max}-V_{min})$.

In the example in FIG. 4, the constructed image also contains two circular arcs 22, 24 (here on the exterior of the annulus, i.e. of radius strictly larger than the outside radius of the annulus $R_e$) the angular extent of which respectively corresponds to the tilt of the frame and to the wrap of the frame, for example in each case in comparison to a maximum value and to a minimum value that are stored in the remote database for the parameter in question.

According to one envisionable variant, other measured parameters could be represented in the image in FIG. 4.

Figure 5:
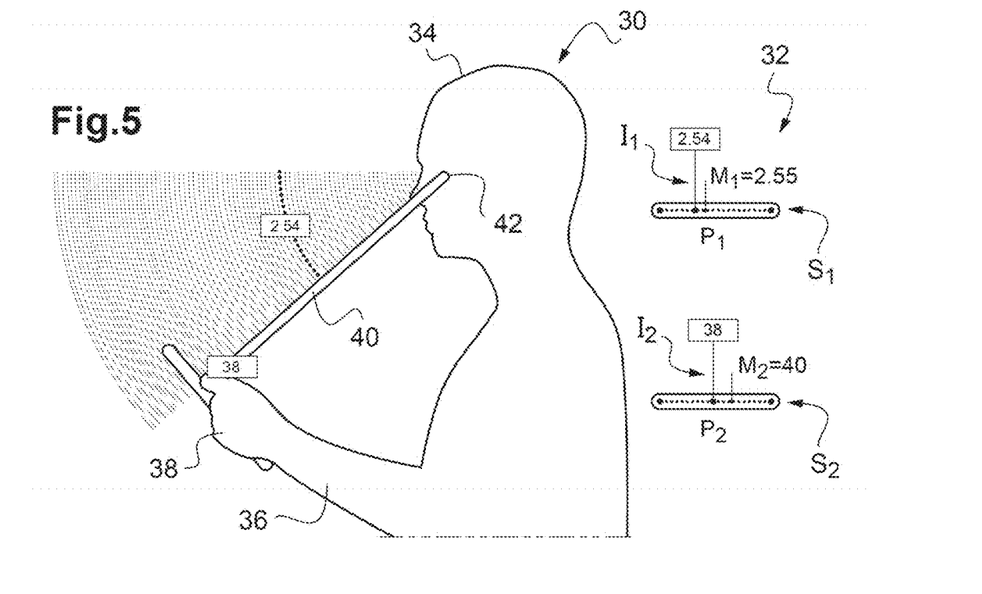
FIG. 5 shows a second exemplary image to be displayed on the screen of the tablet.

A second exemplary image to be displayed on the screen of the tablet TAB is shown in FIG. 5.

The image in FIG. 5 comprises two portions 30, 32.

The first portion 30 includes an illustration of at least one parameter (here two parameters $P_1$, $P_2$: reading distance and vertical angle of inclination of the head). For example, regarding the reading distance $P_1$, the first portion 30 contains the representation of the upper portions of the body of a wearer in the reading position, especially his head 34 (here in cross section in the sagittal plane of the wearer), one forearm 36 and one hand 38, and a segment 40 between his head 34 (more precisely the eye rotation center 42) and the hand 38. On a portion of the segment, here level with the hand, a numerical representation of the measured value is optionally indicated.

The second portion 32 includes, here for each represented parameter $P_1$, $P_2$, a segment $S_1$, $S_2$ corresponding to a range of values of the parameter in question $P_1$, $P_2$, which range is bounded by an upper bound and a lower bound, and an indication $I_1$, $I_2$ level with a point of the segment $S_1$, $S_2$ placing the measured value of the parameter in question in the range of values.

The upper and lower bounds for example respectively correspond to the maximum and minimum values stored in the remote database for the parameter in question. They may thus vary in real time, as measurements of equipment-wearing wearers are successively taken in a shop, a group of shops or even on a larger scale as indicated above. As a variant, the upper and lower bounds could be fixed and predefined.

The indication $I_1$, $I_2$ for example takes the form of a vertical line that extends from the point of the segment corresponding to the measured value of the parameter; in the example in FIG. 5, provision has also been made to include the numerical value of the measured value at the top of the vertical line.

Provision may also be made to include, level with the segment illustrating the range of values, an indication of an average value $M_1$, $M_2$ of the parameter in question, for example the median value of all the values memorized in the remote database.

Figure 6:
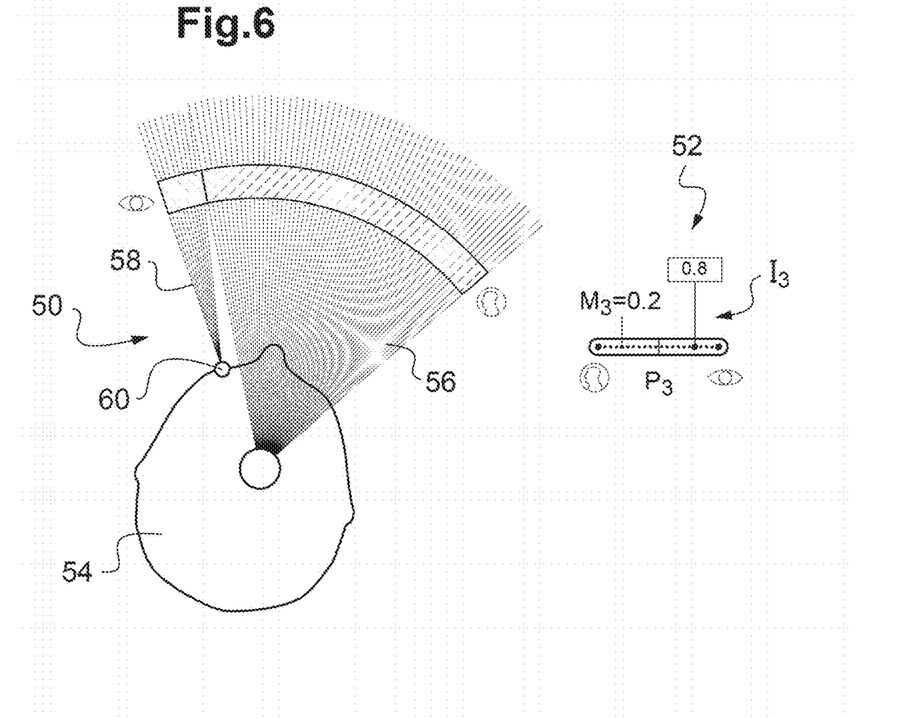
FIG. 6 shows a third exemplary image to be displayed on the screen of the tablet.

A third exemplary image to be displayed on the screen of the tablet TAB is shown in FIG. 6.

The image in FIG. 6 comprises two portions 50, 52.

The first portion 50 includes an illustration of a parameter $P_3$ representative of a behavior when following a movement. Here, the first portion contains a representation of the head 54 of a wearer as seen from above. The first portion 50 furthermore includes a first angular sector 56 centered on the center of the head (which represents the propensity to move the head) and a second angular sector 58 that is partially juxtaposed with the first angular sector and centered on one eye 60 (which represents the propensity to move the eyes).

The second portion 52 includes a segment $S_3$ corresponding to a range of values of the aforementioned representative parameter, which range is bounded by an upper bound (here the value 1) and a lower bound (here the value 0), and an indication $I_3$ level with a point of the segment placing the measured value of the parameter in question in the range of values (in the present case a measured value of 0.8 in the example shown in FIG. 6, which value indicates that the wearer is more an eye mover).

The indication $I_3$ here takes the form of a vertical line that extends from the point of the segment corresponding to the measured value of the parameter; in the example in FIG. 6, provision has also been made to include the numerical value of the measured value at the top of the vertical line.

Provision may also be made to include, level with the segment illustrating the range of values, an indication of an average value $M_3$ of the parameter in question, for example the median value of all the values memorized in the remote database.

Figure 7:
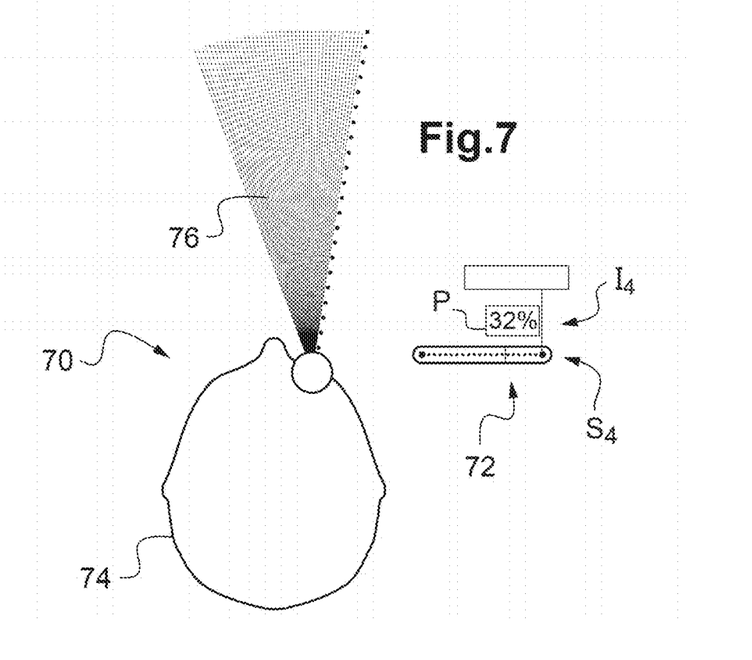
FIG. 7 shows a fourth exemplary image to be displayed on the screen of the tablet.

A fourth exemplary image to be displayed on the screen of the tablet TAB is shown in FIG. 7.

The image in FIG. 7 comprises two portions 70, 72.

The first portion 70 includes an illustration of the dominant eye. Here, the first portion 70 contains a representation of the head 74 of a wearer as seen from above and an angular sector 76 centered on one eye.

The second portion 72 includes a segment $S_4$ on which is represented the distribution of the measurements stored in the remote database, namely here the distribution between dominant right eye and dominant left eye, and an indication $I_4$ of the result of the measurement performed in step E6 regarding the dominant eye.

The indication $I_4$ here takes the form of a vertical line that extends from one end of the segment corresponding to the dominant eye determined in step E6 (right end if the right eye was determined to be dominant, left end if the left eye was determined to be dominant).

Provision may also be made to present in numbers the proportion P (in percent) of the population for which the dominant eye is the same as that of the wearer.

After one or more images such as described above have been displayed, it is possible to implement in step E14 a simulation of the obtained correction, for example in the case of standard eyeglasses and in the case of progressive eyeglasses personalized depending on the values measured in step E6.

To do this, a first distorted image the distortion of which corresponds to that created by the ametropia of the wearer and corrected by means of standard eyeglasses adapted to this ametropia is displayed for example in a first portion of the screen, and a second distorted image the distortion of which corresponds to that created by the ametropia of the wearer and corrected by means of progressive eyeglasses adapted to this ametropia and personalized depending on at least certain of the values measured in step E6 is displayed in a second portion of the screen.

Thus, the wearer may choose a frame and eyeglasses while being fully and clearly informed of the suitability of these items to the morphologico-geometric characteristics of his face, to his visual behavior and to the correction that he requires. Once he has made his choice, the eyeglasses are ordered.

Lastly, in order for the wearer to be able to re-access the measurements that were just performed (for example when he visits another shop of the same chain or an online shop), in step E16 a document, or passport, that bears a data matrix designating the identifier of the wearer in the remote database is printed. As a variant, the data matrix could be replaced by a barcode, or any other representation of the identifier (for example it could take the form of a set of numbers and/or letters).

The document may furthermore include an illustration presenting the values measured in step E6, for example the image shown in FIG. 4 and described above.

Depending on the values measured in step E6 for certain parameters (for example a large frame wrap angle in the case where a strong correction is required and/or a representative parameter $P_3$ indicating that the wearer is an eye mover), it is determined whether and which checking steps will be required on delivery of the frame equipped with the chosen eyeglasses.

When it is necessary to check the suitability of the equipped frame in near vision, the method described in FIG. 3 is for example carried out.

Specifically, FIG. 3 shows a method for displaying a reading test of suitable size.

This method starts in step E20 with the retrieval of the reading distance measured during the prior visit of the wearer when the frame was chosen (measurement of step E6 described below).

To do this, the wearer for example presents the document (passport) that he received during his prior visit (see step E16 described above), thereby allowing the identifier of the user to be obtained by reading the data matrix present on this document.

By virtue of the identifier, the computer ORD may contact the remote server SERV and obtain the measured reading distance associated with this identifier in the remote database.

The computer ORD then transmits the measured reading distance to the tablet TAB that scales, in step E22 (by magnification or reducing), a standardized reading test (for example of the Parinaud type) so that, when the wearer holds the tablet TAB in his hands (at a distance from his eye rotation center that is assumed to be equal to that measured during the prior visit), the dimensions of the reading test seen by the wearer are the same as those that it has when at the standard reading test distance (for example 33 cm).

In practice, the standardized reading test is for example magnified by a factor $d_{mes}/d_{std}$ (where $d_{mes}$ is the reading distance measured in step E6 and retrieved in step E20 and $d_{std}$ is the standard distance of the reading test), a magnifying factor lower than 1 implying a reduction in the size of the symbols of the standardized test.

The scaled reading test is displayed on the screen of the tablet TAB in step E24. Thus, the wearer performs his reading test in a natural position, for which his eyeglasses were where relevant designed.

The invention claimed is:

1. A method for accompanying a choice of a piece of visual equipment which includes at least one ophthalmic eyeglass and a spectacle frame of a future wearer, the method comprising:
a step in which an electronic apparatus receives at least one first datum representative of a first distance measured between one eye of the wearer and the frame, and a second datum representative of a second distance measured between the eye of the wearer and the frame;
a step in which the electronic apparatus determines a first width associated with the first datum, by comparing the first datum to a first lower bound and a first upper bound of a first range of values that is associated with the first distance represented by the first datum, and in which the electronic apparatus determines a second width associated with the second datum by comparing the second datum to a second lower bound and a second upper bound of a second range of values that is associated with the second distance represented by the second datum;
a step in which an image comprising a first section having the first width and a second section having the second width is constructed, the first section and the second section being juxtaposed in the image.

2. The method as claimed in claim 1, wherein the first distance is a distance, along a horizontal axis parallel to a sagittal plane of the wearer, between the eye rotation center of the wearer and a point of the frame or a positional point of a corrective eyeglass of said eye in the frame.

3. The method as claimed in claim 1, wherein said eye is the left eye of the wearer, wherein the first section is an annular section formed in a first angular sector located in a left-hand portion of the image and wherein the second section is an annular section formed in a second angular sector located in the left-hand portion of the image.

4. The method as claimed in claim 1, wherein the constructed image comprises an annulus-shaped graduated scale the outside radius of which corresponds to the first upper bound in the first angular sector and to the second upper bound in the second angular sector.

5. The method as claimed in claim 1,
wherein the receiving step comprises the reception of a third datum representative of a third distance measured between the right eye of the wearer and the frame and of a fourth datum representative of a fourth distance measured between the right eye of the wearer and the frame,
wherein the determining step comprises determining a third width and a fourth width, respectively associated with the third datum and the fourth datum, by comparing each datum to the lower and upper bounds of a range of values that is associated with the distance represented by the datum in question, and
wherein the constructed image comprises a third annular section having the third width in a third angular sector located in a right-hand portion of the image and a fourth annular section having the fourth width in a fourth angular sector located in the right-hand portion of the image.

6. The method as claimed in claim 1, further comprising:
a step of measuring the first distance and second distance by means of a measurement-taking device.

7. The method as claimed in claim 1, further comprising:
a step of displaying the constructed image on a screen, wherein the first upper bound and the first lower bound are respectively the maximum value and the minimum value of the first distance encountered in a given population,
wherein the second upper bound and the second lower bound are respectively the maximum value and the minimum value of the second distance encountered in the given population.

8. The method as claimed in claim 1, wherein the second distance is a distance between the pupil of the eye of the wearer and a median point of the frame along a horizontal axis perpendicular to the sagittal plane of the wearer.

9. The method as claimed in claim 8,
wherein said eye is the left eye of the wearer,
wherein the first section is an annular section formed in a first angular sector located in a left-hand portion of the image and wherein the second section is an annular section formed in a second angular sector located in the left-hand portion of the image,
wherein the receiving step comprises the reception of a third datum representative of a third distance measured between the right eye of the wearer and the frame and of a fourth datum representative of a fourth distance measured between the right eye of the wearer and the frame,
wherein the determining step comprises determining a third width and a fourth width, respectively associated with the third datum and the fourth datum, by comparing each datum to the lower and upper bounds of a range of values that is associated with the distance represented by the datum in question,
wherein the constructed image comprises a third annular section having the third width in a third angular sector located in a right-hand portion of the image and a fourth annular section having the fourth width in a fourth angular sector located in the right-hand portion of the image,
wherein the fourth distance is a distance between the pupil of the right eye and the median point of the frame along the horizontal axis perpendicular to the sagittal plane of the wearer, and
wherein the second angular sector and the fourth angular sector are located on either side of a horizontal direction of the image.

10. The method as claimed in claim 1,
wherein the receiving step comprises the reception of a fifth datum representative of a fifth distance measured between the left eye of the wearer and the frame and of a sixth datum representative of a sixth distance measured between the right eye of the wearer and the frame,
wherein the determining step comprises determining a fifth width and a sixth width, respectively associated with the fifth datum and the sixth datum, by comparing each datum to the lower and upper bounds of a range of values that is associated with the distance represented by the datum in question, and
wherein the constructed image comprises a fifth annular section having the fifth width in a fifth angular sector located in the left-hand portion of the image and a sixth annular section having the sixth width in a sixth angular sector located in the right-hand portion of the image.

11. The method as claimed in claim 10, wherein the fifth distance is a distance between the pupil of the left eye and a predefined point of the frame along a vertical axis, and
wherein the sixth distance is a distance between the pupil of the right eye and the predefined point of the frame along said vertical axis.

12. The method as claimed in claim 1, wherein the image comprises a circular arc the angular extent of which is determined by a characteristic angle of the frame.

13. The method as claimed in claim 12, wherein the characteristic angle represents the tilt of the frame or the wrap of the frame.

14. The method as claimed in claim 1, wherein the constructed image comprises the representation on an orthonormal coordinate system of the coordinates of the eye rotation center.

15. The method as claimed in claim 1,
wherein the steps of receiving, determining and constructing are implemented by a remote computer, and
wherein a programmable device sends the first datum and the second datum to the remote computer and receives the constructed image from the remote computer for display on a screen.

16. A device for accompanying a choice of a piece of equipment which includes at least one ophthalmic eyeglass and a spectacle frame of a future wearer of said piece of equipment, the device comprising:
a module for receiving at least one first datum representative of a first distance measured between one eye of the wearer and the frame, and a second datum representative of a second distance measured between the eye of the wearer and the frame;
a module for determining a first width associated with the first datum by comparing the first datum to a first lower bound and a first upper bound of a first range of values that is associated with the first distance represented by the first datum, and for determining a second width associated with the second datum by comparing the second datum to a second lower bound and a second upper bound of a second range of values that is associated with the second distance represented by the second datum;
a module for constructing an image comprising a first section having the first width and a second section having the second width, the first section and the second section being juxtaposed in the image.

* * * * *